United States Patent [19]
Candau et al.

[11] Patent Number: 6,060,041
[45] Date of Patent: May 9, 2000

[54] PHOTOPROTECTIVE COSMETIC COMPOSITIONS CONTAINING A METAL OXIDE NANOPIGMENT AND AN ACRYLIC TERPOLYMER, AND USE OF THESE COMPOSITIONS FOR PROTECTING KERATINOUS MATERIAL AGAINST ULTRAVIOLET RADIATION

[75] Inventors: Didier Candau, Bievres, France; Isabelle Hansenne, Westfield, N.J.

[73] Assignee: L'Oreal, Paris, France

[21] Appl. No.: 09/332,007

[22] Filed: Jun. 14, 1999

[30] Foreign Application Priority Data

Jun. 15, 1998 [FR] France .................... 98 07511

[51] Int. Cl.[7] .............................. A61K 7/42; A61K 7/44; A61K 7/00
[52] U.S. Cl. .................. 424/59; 424/60; 424/400; 424/401
[58] Field of Search .............. 424/59, 60, 400, 424/401

[56] References Cited

U.S. PATENT DOCUMENTS

| | | | |
|---|---|---|---|
| 5,015,711 | 5/1991 | Simonet et al. | 526/301 |
| 5,066,710 | 11/1991 | Simonet et al. | 524/555 |
| 5,294,693 | 3/1994 | Egraz et al. | 526/310 |
| 5,362,415 | 11/1994 | Egraz et al. . | |

FOREIGN PATENT DOCUMENTS

| | | |
|---|---|---|
| 0173109 | 3/1986 | European Pat. Off. . |
| 0350414 | 1/1990 | European Pat. Off. . |
| 0577526 | 1/1994 | European Pat. Off. . |
| WO93/04665 | 3/1993 | WIPO . |
| WO93/24544 | 12/1993 | WIPO . |

*Primary Examiner*—Shelley A. Dodson
*Attorney, Agent, or Firm*—Jacobson, Price, Holman & Stern, PLLC

[57] ABSTRACT

The present application relates to photoprotective cosmetic compositions containing at least one metal oxide nanopigment and an acrylic terpolymer, as well as to the use of these compositions to protect the skin, the hair, the eyelashes, the eyebrows or mucous membranes against ultraviolet radiation.

The acrylic terpolymer comprises:
a) about 20 to 70% by weight of a carboxylic acid containing $\alpha$, $\beta$-monoethylenic unsaturation,
b) about 20 to 80% by weight of a non-surfactant monomer containing monoethylenic unsaturation, which is different from a), and
c) about 0.5 to 60% by weight of a nonionic urethane monomer which is the product of reaction of a monohydric nonionic surfactant with a monoisocyanate containing monoethylenic unsaturation.

The metal oxide nanopigments are chosen in particular from coated or uncoated titanium, cerium, zirconium, iron and zinc oxide nanopigments, or mixtures thereof, and have an elementary particle size of greater than 5 nm and less than 100 nm.

31 Claims, No Drawings

PHOTOPROTECTIVE COSMETIC COMPOSITIONS CONTAINING A METAL OXIDE NANOPIGMENT AND AN ACRYLIC TERPOLYMER, AND USE OF THESE COMPOSITIONS FOR PROTECTING KERATINOUS MATERIAL AGAINST ULTRAVIOLET RADIATION

The present invention relates to photoprotective cosmetic compositions containing at least one metal oxide nanopigment and an acrylic terpolymer, as well as to the use of these compositions for protecting keratinous material, in particular the skin or the hair, against ultraviolet radiation.

It is known that light radiation with wavelengths of between 280 nm and 400 nm permit tanning of the human epidermis and that rays with wavelengths of between 280 nm and 320 nm, known as UV-B rays, cause skin burns and erythema which can harm the development of a natural tan; this UV-B radiation should thus be screened out.

It is also known that UV-A rays, with wave-lengths of between 320 nm and 400 nm, which cause tanning of the skin, are liable to induce an adverse change therein, in particular in the case of sensitive skin or skin which is continuously exposed to solar radiation. UV-A rays in particular cause a loss of skin elasticity and the appearance of wrinkles, leading to premature ageing. They promote the triggering of the erythemal reaction or amplify this reaction in certain individuals and may even be the cause of phototoxic or photoallergic reactions. It is thus desirable also to screen out UV-A radiation.

Many organic sunscreens capable of more or less selectively absorbing harmful UV-A and/or UV-B rays have been proposed to date in the cosmetics field.

However, it is sought to lower the concentration of synthetic organic sunscreens, which can give rise to unfavourable side effects on the body, by replacing them totally or partially with inorganic pigments and in particular with metal oxide nanopigments such as titanium, cerium, zirconium, zinc and iron oxides.

The addition of metal oxide nanopigments also makes it possible to increase the photoprotective power of cosmetic compositions containing standard UV screening agents.

Consumers are increasingly keen to use light, easy-to-apply cosmetic compositions in the form of a thickened liquid such as a milk, a cream, a gel or a cream-gel. This type of presentation is a practical preoccupation for users: facilitating the removal of the product from its packaging without any significant loss, limiting the diffusion of the product to the local area of application and being able to use amounts that are sufficient to obtain the desired effect.

However, in this type of support, and in particular in supports of the cream-gel type, which are particularly pleasant from a cosmetic viewpoint since they contain no standard emulsifier, it is difficult to introduce nanopigments which give a homogeneous, stable emulsion. Poor dispersion of the nanopigments is observed in supports containing, for example, as thickening-gelling agent, a polymer containing in its chain a hydrophilic part and a hydrophobic part consisting of a fatty chain, for instance the product "Pemulen TR1" sold by the company Goodrich.

The Applicant has discovered, surprisingly, and this forms the subject of the present invention, a novel family of thickening and/or gelling polymers which makes it possible to obtain homogeneous, stable cosmetic compositions containing metal oxide nanopigments by improving the dispersion of these nanopigments in the supports used.

The subject of the present invention is thus cosmetic compositions for protecting, in particular, the skin or the hair against ultraviolet radiation and containing, in a cosmetically acceptable aqueous support, at least one metal oxide nanopigment and an acrylic terpolymer which will be defined in greater detail later in the description.

This polymer makes it possible in particular to prepare aqueous or aqueous-organic compositions containing cosmetically acceptable solvents, ranging from slightly gelled products to products of very thick consistency.

The advantages of this terpolymer are that it is stable in electrolytic medium and has very good thickening power at a pH equal to or above 5.5, making it possible to achieve a good level of viscosity and to be able to use high concentrations of alcohol.

This polymer makes it possible to prepare homogeneous gels which are easy to spread, soft and slippery when applied, and are stable on storage.

The acrylic terpolymer used in accordance with the invention is soluble or swellable in alkalis. It is characterized in that it comprises:

a) about 20 to 70% by weight, preferably 25 to 55% by weight, of a carboxylic acid containing $\alpha$, $\beta$-monoethylenic unsaturation;

b) about 20 to 80% by weight, preferably 30 to 65% by weight, of a non-surfactant monomer containing monoethylenic unsaturation, which is different from a), and c) about 0.5 to 60% by weight, preferably 10 to 50% by weight, of a nonionic urethane monomer which is the product of reaction of a monohydric nonionic surfactant with a monoisocyanate containing monoethylenic unsaturation.

The carboxylic acid containing $\alpha$, $\beta$-monoethylenic unsaturation a) can be chosen from many acids and in particular acrylic acid, methacrylic acid, itaconic acid and maleic acid. Methacrylic acid is preferred. A large proportion of acid is essential in order to give a polymer structure which dissolves and gives a thickening effect by reaction with an alkaline compound such as sodium hydroxide, alkanolamines, aminomethylpropanol or aminomethylpropanediol.

The terpolymer should also contain a large proportion, indicated above, of a monomer b) containing monoethylenic unsaturation which has no surfactant properties. The preferred monomers are those which give polymers that are water-insoluble when they are homopolymerized and are illustrated by $C_1$–$C_4$ alkyl acrylates such as methyl acrylate, ethyl acrylate and butyl acrylate, or corresponding methacrylates. The monomers more particularly preferred are methyl and ethyl acrylates. Other monomers which can be used are styrene, vinyltoluene, vinyl acetate, acrylonitrile and vinylidene chloride. Non-reactive monomers are preferred, such monomers being those in which the single ethylenic group is the only group which is reactive under the polymerization conditions. However, monomers which contain groups that are reactive under the action of heat can be used in certain situations, such as hydroxyethyl acrylate.

The monohydric nonionic surfactants used to obtain the nonionic urethane monomer c) are well known and are generally alkoxylated hydrophobic compounds containing an alkylene oxide forming the hydrophilic part of the molecule. The hydrophobes generally consist of an aliphatic alcohol or an alkylphenol in which a carbon chain containing at least six carbon atoms constitutes the hydrophobic part of the surfactant.

The preferred monohydric nonionic surfactants have the formula:

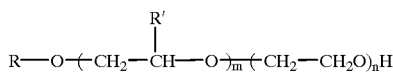

in which R is a $C_6$–$C_{30}$ alkyl or $C_8$–$C_{30}$ aralkyl group, R' is a $C_1$–$C_4$ alkyl group, n is an average number ranging approximately from 5 to 150 and m is an average number ranging approximately from 0 to 50, with the condition that n is at least as large as m and that n+m=5–150.

As preferred $C_6$–$C_{30}$ alkyl groups, mention may be made of dodecyl and $C_{18}$–$C_{26}$ alkyl radicals. As aralkyl groups, mention may be made more particularly of ($C_8$–$C_{13}$) alkylphenyl groups. The preferred group R' is the methyl group.

The monoisocyanate containing monoethylenic unsaturation which is used to form the nonionic urethane monomer c) can be chosen from a wide variety of compounds. A compound containing any copolymerizable unsaturation such as an acrylic or methacrylic unsaturation can be used. An allylic unsaturation imparted by allyl alcohol can also be used. The preferred monoethylenic monoisocyanate is α,α-dimethyl-m-isopropenyl-benzylisocyanate.

The acrylic terpolymer defined above is obtained by an aqueous emulsion copolymerization of the components a), b) and c) which is entirely common and described in patent application EP-A-0,173,109.

As terpolymers which can be used according to the invention, mention may be made of the product of reaction of methacrylic acid as component a), of ethyl acrylate as component b) and of a nonionic urethane macromonomer as component c), having the following structure:

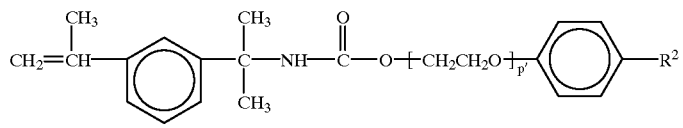

in which p' ranges from 6 to 150 and is preferably equal to 30 and $R^2$ is a $C_8$–$C_{13}$ alkyl radical, such as that described in Example 3 of patent application EP-A-0,173,109.

The preferred acrylic terpolymer used according to the invention is obtained from methacrylic acid as component a), methyl acrylate as component b) and a nonionic urethane macromonomer as component c), having the following structure:

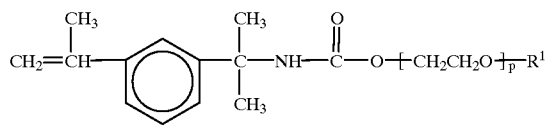

in which p ranges from 6 to 150 and $R^1$ is a $C_{18}$–$C_{26}$ alkyl radical, preferably $C_{20}$–$C_{24}$, linear, of plant origin, such as the docosyl radical.

The acrylic terpolymer is present in the photoprotective cosmetic compositions of the invention in concentrations ranging from 0.01 to 10% by weight relative to the total weight of the composition, and preferably from 0.1 to 5% by weight.

The compositions in accordance with the invention also contain at least one metal oxide nanopigment chosen from titanium, cerium, zirconium, zinc and iron oxides, or mixtures thereof.

The term nanopigment is understood to refer to a pigment whose average elementary particle size is greater than 5 nm and less than 100 nm. According to a preferred embodiment of the invention, this size is less than 50 nm.

The nanopigments can be coated or non-coated.

The coated pigments are pigments which have undergone one or more surface treatments of chemical, electronic, mechanochemical and/or mechanical nature with compounds as described, for example, in Cosmetics & Toiletries, February 1990, Vol. 105, pp. 53–64, such as amino acids, beeswax, fatty acids, fatty alcohols, anionic surfactants, lecithins, sodium, potassium, zinc, iron or aluminium salts of fatty acids, metal alkoxides (titanium or aluminium alkoxides), polyethylene, silicones, proteins (collagen, elastin), alkanolamines, silicon oxides, metal oxides or sodium hexametaphosphate.

In a known manner, the silicones are organosilicon polymers or oligomers of linear or cyclic, branched or unbranched structure of variable molecular weight, obtained by polymerization and/or polycondensation of suitably functionalized silanes, and consisting essentially of a repetition of main units in which the silicon atoms are linked together via oxygen atoms (siloxane bond), optionally substituted hydrocarbon-based radicals being directly linked via a carbon atom to the said silicon atoms.

The term "silicones" also encompasses the silanes required for their preparation, in particular alkylsilanes.

The silicones used to coat the nanopigments which are suitable for the present invention are preferably chosen from the group containing alkylsilanes, polydialkylsiloxanes and polyalkylhydrogenosiloxanes. Even more preferably, the silicones are chosen from the group containing octyltrimethylsilane, polydimethylsiloxanes and polymethylhydrogenosiloxanes.

Needless to say, before their treatment with silicones, the metal oxide nanopigments may have been treated with other surface agents, in particular with cerium oxide, alumina, silica, aluminium compounds, silicon compounds or mixtures thereof.

The coated pigments are more particularly titanium oxides coated with:

silica, such as the product "Sunveil" from the company Ikeda, silica and iron oxide, such as the product "Sunveil F" from the company Ikeda, silica and alumina, such as the products "Micro-titanium Dioxide MT 500 SA" and "Microtitanium Dioxide MT 100 SA" from the company Tayca, and "Tioveil" from the company Tioxide, alumina, such as the products "Tipaque TTO-55 (B)" and "Tipaque TTO-55 (A)" from the company Ishihara, and "UVT 14/4" from the company Kemira, alumina and aluminium stearate, such as the product "Microtitanium Dioxide MT 100 T, MT 100 TX and MT 100 Z" from the company Tayca, alumina and aluminium laurate, such as the product "Microtitanium Dioxide MT 100 S" from the company Tayca, iron oxide and iron stearate, such as the product "Microtitanium Dioxide MT 100 F" from the company Tayca, zinc oxide and zinc stearate, such as the product "BR 351" from the company Tayca, silica and alumina, and treated with a silicone, such as the products "Microtitanium Dioxide MT 600 SAS", "Microtitanium Dioxide MT 500 SAS" or "Microtitanium Dioxide MT 100 SAS" from the company Tayca, silica, alumina and aluminium stearate, and treated with a silicone, such as the product "STT-30-DS" from the company Titan Kogyo, alumina and treated with a silicone, such as the products "Tipaque TTO-55 (S)" from the company Ishihara or "UV Titan M 262" from the company Kemira, triethanolamine, such as the product "STT-65-S" from the company Titan Kogyo, stearic acid, such as the product "Tipaque TTO-55 (C)" from the company Ishihara, sodium hexametaphosphate, such as the product "Microtitanium dioxide MT 150 W" from the company Tayca.

Other titanium oxide nanopigments treated with a silicone are preferably $TiO_2$ treated with octyl trimethylsilane and whose mean elementary particle size is between 25 and 40 nm, such as the product sold under the trade name "T 805" by the company Degussa Silices, $TiO_2$ treated with a polydimethylsiloxane and whose mean elementary particle size is 21 nm, such as the product sold under the trade name "70250 Cardre UF $TiO_2SI3$" by the company Cardre, anatase/rutile $TiO_2$ treated with a polydimethylhydrogenosiloxane and whose mean elementary particle size is 25 nm, such as the product sold under the trade name "Microtitanium Dioxide USP Grade Hydrophobic" by the company Color Techniques.

Mention may also be made of mixtures of metal oxides, in particular of titanium dioxide and of cerium dioxide, including the equivalent-weight mixture of silica-coated titanium dioxide and cerium dioxide, sold by the company Ikeda under the name "Sunveil A", as well as the mixture of titanium dioxide and zinc dioxide coated with alumina, silica and silicone, such as the product "M 261" sold by the company Kemira, or coated with alumina, silica and glycerol, such as the product "M 211" sold by the company Kemira.

The non-coated titanium oxides are sold, for example, by the company Tayca under the trade names "Microtitanium Dioxide MT 500 B" or "Microtitanium Dioxide MT 600 B", by the company Degussa under the name "P 25", by the company Wacker under the name "Transparent Titanium Oxide PW", by the company Miyoshi Kasei under the name "UFTR", by the company Tomen under the name "ITS" and by the company Tioxide under the name "Tioveil AQ".

The non-coated zinc oxides are sold, for example, by the company Sumitomo under the name "Ultra Fine Zinc Oxide Powder", by the company Presperse under the name "Finex 25" or by the company Ikeda under the name "MZO-25" or by the company Sunsmart under the name "Z-Cote".

The coated zinc oxides are sold, for example, under the name "Z-Cote HP1" by the company Sunsmart.

The non-coated cerium oxide is sold under the name "Colloidal Cerium Oxide" by the company Rhône-Poulenc.

The non-coated iron oxides are sold, for example, by the company Arnaud under the names "Nanogard WCD 2002 (FE 45B)", "Nanogard Iron FE 45 BL AQ", "Nanogard FE 45R AQ", "Nanogard WCD 2006 (FE 45R)" or by the company Mitsubishi under the name "TY-220".

The coated iron oxides are sold, for example, by the company Arnaud under the names "Nanogard WCD 2008 (FE 45B FN)", "Nanogard WCD 2009 (FE 45B 556)", "Nanogard FE 45 BL 345", "Nanogard FE 45 BL" or by the company BASF under the name "Transparent Iron Oxide".

According to the invention, coated or non-coated titanium oxide nanopigments are particularly preferred.

The titanium oxide can be in rutile, anatase or amorphous form, but preferably in rutile and/or anatase form.

The nanopigments can be present in the compositions in accordance with the invention in concentrations which are generally between 0.1% and 30% by weight, and preferably between 0.5% and 10% by weight, relative to the total weight of the composition.

Besides the nanopigments, the compositions according to the invention can also contain uncoloured standard pigments with a usual particle size of between 100 and 700 nm, such as zinc oxide, titanium dioxide "F. F. Hombitan" of mean elementary particle size 400 nm, sold by the company Sachtleben Chemie GmbH, zinc oxide "Neige" sold by the company Lambert Rivière, or coloured pigments such as the iron oxides "FDC Red 40 (37011/90119)" sold by the company Anstead, "Sicomet Brown ZP 3569" and "Sicovit Yellow 10 E 172" sold by the company BASF.

Needless to say, the cosmetic compositions according to the invention can contain one or more hydrophilic or lipophilic organic sunscreens which absorb in the UV-A and/or UV-B range. These screening agents can be chosen in particular from cinnamates, salicylates, benzylidene camphor derivatives, triazine derivatives, benzophenone derivatives, benzotriazole derivatives, β,β-diphenylacrylate derivatives, dibenzoylmethane derivatives, p-aminobenzoates, and the screening polymers and screening silicones described in application WO 93/04665. Other examples of organic screening agents are given in patent application EP-A-0,487,404. These organic screening agents can be present in the compositions according to the invention at concentrations of between 0.1 and 30% by weight relative to the total weight of the composition.

The compositions according to the invention can also contain artificial tanning and/or browning agents for the skin (self-tanning agents) such as, for example, dihydroxyacetone (DHA).

The compositions according to the invention contain a cosmetically acceptable aqueous medium. They have a pH which can range from 3.5 to 11, preferably between 5.5 and 11 and even more preferably between 5.5 and 8.5.

The cosmetically acceptable medium for the compositions according to the invention consists more particularly of water and optionally of cosmetically acceptable organic solvents.

The organic solvents can represent from 0.5 to 90% of the total weight of the composition. They can be chosen from the group consisting of hydrophilic organic solvents, lipophilic organic solvents, amphiphilic solvents or mixtures thereof.

Among the hydrophilic organic solvents, mention may be made, for example, of linear or branched lower monoalcohols having from 1 to 8 carbon atoms, polyethylene glycols having from 6 to 80 ethylene oxide units, and polyols.

As amphiphilic organic solvents, mention may be made of polypropylene glycol (PPG) derivatives, such as esters of polypropylene glycol and of fatty acid, derivatives of PPG and of fatty alcohol, such as PPG-23 oleyl ether, and PPG-36 oleate.

As lipophilic organic solvents, mention may be made, for example, of fatty esters such as diisopropyl adipate, dioctyl adipate, alkyl benzoates and dioctyl malate.

In order for the cosmetic compositions of the invention to be more pleasant to use (softer when applied, more nourishing and more emollient), it is possible to add a fatty phase to the medium of these compositions.

The fatty phase can represent up to 50% of the total weight of the composition.

This fatty phase can contain an oil or a wax or mixtures thereof, and can also comprise fatty acids, fatty alcohols and fatty acid esters. The oils can be chosen from animal, plant, mineral or synthetic oils and in particular from liquid petroleum jelly, liquid paraffin, isoparaffins, poly-β-olefins, fluoro oils and perfluoro oils. Similarly, the waxes can be chosen from animal, fossil, plant, mineral or synthetic waxes which are known per se.

The compositions of the invention can contain adjuvants that are common in the cosmetics field, such as other standard gelling agents and/or thickeners; other anionic polymers; surfactants; moisturizers; emollients; hydrophilic or lipophilic active agents such as ceramides; anti-free-radical agents; sequestering agents; antioxidants; preserving agents; acidifying or basifying agents; fragrances; fillers; dyestuffs; modified or non-modified, volatile or non-volatile silicones; reducing agents. The amounts of these various adjuvants are those used conventionally in the fields considered.

Needless to say, a specialist will take care to select the optional compound(s) to be added to the composition according to the invention such that the advantageous properties intrinsically associated with the composition in accordance with the invention are not, or are not substantially, adversely affected by the addition envisaged.

The compositions according to the invention can be in any form which is suitable for topical application, in particular in the form of lotions, vesicle dispersions, simple or complex emulsions (O/W, W/O, O/W/O, W/O/W) such as creams or milks, aqueous or aqueous-alcoholic gels, or cream-gels, in the form of powders, pastes, and can optionally be packaged as an aerosol and can be in the form of mousses or sprays. Preferably, these compositions are in the form of a cream-gel. They are prepared according to the usual methods.

The cosmetic compositions of the invention can be used as compositions for protecting the human epidermis or the hair against ultraviolet rays, as antisun compositions or as make-up products.

When the cosmetic composition according to the invention is used to protect the human epidermis against UV rays, or as an antisun composition, it can be in the form of a suspension or dispersion in solvents or fatty substances, in the form of a nonionic vesicle dispersion or alternatively in the form of an emulsion, such as a cream or a milk, or in the form of an ointment, a gel, a cream-gel, an aerosol mousse or a spray.

When the cosmetic composition according to the invention is used to protect the hair, it can be in the form of a lotion, a gel, an emulsion or a nonionic vesicle dispersion and can constitute, for example, a shampoo, a rinse-out composition, to be applied before or after shampooing, before or after dyeing or bleaching, before, during or after permanent-waving or straightening the hair, a styling or treating lotion or gel, a blow-drying or hairsetting lotion or gel, or a permanent-waving, staightening, dyeing or bleaching composition for the hair.

When the composition is used as a make-up product for the eyelashes, the eyebrows or the skin, such as a foundation, a stick of lipstick, an eyeshadow, a blusher, a mascara or an eyeliner, it can be in solid or pasty, anhydrous or aqueous form, such as oil-in-water or water-in-oil emulsions, nonionic vesicle dispersions or alternatively suspensions.

Another subject of the present invention lies in a cosmetic, non-therapeutic treatment process for the skin, the hair, the eyelashes, the eyebrows or mucous membranes which is intended to protect them against the effects of UV rays, this process consisting in applying an effective amount of a cosmetic composition as defined above to these materials.

Concrete, but in no way limiting, examples illustrating the invention will now be given.

| EXAMPLE 1 : Sun cream-gel | | |
|---|---|---|
| A | ($C_{12}$–$C_{15}$) alkyl benzoate | 25 g |
|   | Mixture of methyl, ethyl, propyl, butyl and isobutyl p-hydroxy-benzoates/2-phenoxyethanol | 1 g |
| B | Rutile titanium oxide (15 nm) treated with aluminium stearate/ alumina, sold under the name "MT 100T" by the company Tayca | 5 g |
| C | Ethoxylated (40 EO) methacrylic acid/methyl acrylate/behenyl dimethylmetaisopropenylbenzyl-isocyanate terpolymer, as an aqueous 25% dispersion | 0.6 g AM |
| E | Triethanolamine | 0.48 g |
| D | Sterilized demineralized water | 65.92 g |

All the steps in the preparation of this cream-gel are carried out under cold conditions.

1—B is dispersed in A using an Ultra Turrax T25 at 10,000 rev/min

2—C and D are weighed out in a beaker

3—The preparation (B+A) is poured into (C+D) while stirring with the Ultra Turrax T25 at 10,000 rev/min 4—E is added and the mixture is homogenized.

A stable, homogeneous cream-gel which spreads well on the skin is obtained.

| COMPARATIVE EXAMPLE 2 : Sun cream-gel | | |
|---|---|---|
| A | ($C_{12}$–$C_{15}$) alkyl benzoate | 25 g |
|   | Mixture of methyl, ethyl, propyl, butyl and isobutyl p-hydroxy-benzoates/2-phenoxyethanol | 1 g |
| B | Rutile titanium oxide (15 nm) treated with aluminium stearate/ alumina, sold under the name "MT 100T" by the company Tayca | 5 g |
| C | Crosslinked acrylic acid/ ($C_{10}$–$C_{30}$) alkyl acrylate copolymer, sold under the name "Pemulen TR1" by the company Goodrich | 0.6 g |
| E | Triethanolamine | 0.6 g |
| D | Sterilized demineralized water | 67.8 g |

All the steps in the preparation of this cream-gel are carried out under cold conditions.

1—B is dispersed in A using an Ultra Turrax T25 at 10,000 rev/min

2—D is added to C while homogenizing with a Moritz Turbo Lab 2100 at 500 rev/min until C has dissolved 3—The preparation (B+A) is poured into (C+D) while stirring with the Ultra Turrax T25 at 10,000 rev/min 4—E is added and the mixture is homogenized.

An unstable, non-homogeneous cream-gel containing large oily globules and large lumps of pigment is obtained.

| EXAMPLE 3 : High-protection sun cream-gel | |
| --- | --- |
| 4-tert-Butyl-4'-methoxydibenzoylmethane ("Parsol 1789" sold by the company Roche) | 2 g |
| Benzene-1,4-di(3-methylidene-10-camphor-sulphonic acid), as an aqueous 33% solution | 1.5 g |
| 2-Ethylhexyl 2-cyano-3,3-diphenylacrylate ("Uvinul N 539" sold by the company BASF) | 10 g |
| Ethoxylated (40 EO) methacrylic acid/methyl acrylate/behenyl dimethylmetaisopropenylbenzylisocyanate terpolymer, as an aqueous 25% dispersion | 3 g AM |
| Titanium dioxide treated with octyltrimethylsilane, sold under the name "T805" by the company Degussa Silices | 5 g |
| Isohexadecane | 10 g |
| 12-Hydroxystearic acid oligomer stearate | 0.5 g |
| Moisturizers | 8 g |
| Sequestering agent   qs | |
| Triethanolamine   qs   pH 7 | |
| Sterilized demineralized water   qs | 100 g |

A homogeneous, stable cream-gel which spreads well on the skin is obtained.

What is claimed is:

1. Cosmetic composition for the photoprotection of keratinous material, comprising in a cosmetically acceptable aqueous medium, at least one metal oxide nanopigment and an acrylic terpolymer comprising:
    a) about 20 to 70% by weight, of a carboxylic acid containing α, β-monoethylenic unsaturation;
    b) about 20 to 80% by weight, of a non-surfactant monomer containing monoethylenic unsaturation, which is different from a); and
    c) about 0.5 to 60% by weight, of a nonionic urethane monomer which is the product of reaction of a monohydric nonionic surfactant with a monoisocyanate containing monoethylenic unsaturation.

2. Composition according to claim 1, wherein the carboxylic acid containing α, β-monoethylenic unsaturation a) is acrylic acid, methacrylic acid, itaconic acid or maleic acid.

3. Composition according to claim 2, wherein the carboxylic acid containing α, β-monoethylenic unsaturation a) is methacrylic acid.

4. Composition according to claim 1, wherein the non-surfactant monomer containing monoethylenic unsaturation b) is $(C_1-C_4)$alkyl acrylates or methacrylates, styrene, vinyltoluene, vinyl acetate, acrylonitrile or vinylidene chloride.

5. Composition according to claim 4, wherein the non-surfactant monomer containing monoethylenic unsaturation is methyl or ethyl acrylate.

6. Composition according to claim 1 wherein the monohydric nonionic surfactant used to obtain the nonionic urethane monomer c) has the formula:

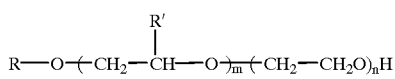

in which R is a $C_6-C_{30}$ alkyl or $C_8-C_{30}$ aralkyl group, R' is a $C_1-C_4$ alkyl group, n is an average number ranging from about 5 to 150 and m is an average number ranging from about 0 to 50, with the condition that n is at least as large as m and that n+m=5–150.

7. Composition according to claim 6, wherein R is a dodecyl, $C_{18}-C_{26}$ alkyl or $(C_8-C_{13})$alkylphenyl groups, m=0 and n is an average number ranging from about 5 to 150.

8. Composition according to claim 1 wherein the monoisocyanate containing monoethylenic unsaturation used to form the nonionic urethane monomer c) is α,α-dimethyl-m-isopropenyl benzyl isocyanate.

9. Composition according to claim 1 wherein the acrylic terpolymer is an aqueous dispersion obtained methacrylic acid as component a), methyl acrylate as component b) and from a nonionic urethane macromonomer of the following structure:

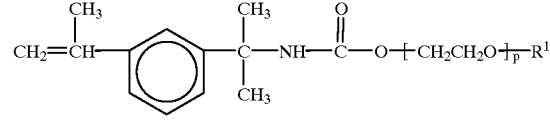

in which p ranges from 6 to 150 and $R^1$ is a $C_{18}-C_{26}$ alkyl radical.

10. Composition according to claim 1 wherein the acrylic terpolymer is present in concentrations ranging from 0.01 to 10% by weight, relative to the total weight of the composition.

11. Composition according to claim 1 wherein the metal oxide nanopigments have a mean elementary particle size of greater than 5 nm and less than 100 nm.

12. Composition according to claim 11, wherein the metal oxide nanopigments have a mean elementary particle size of less than 50 nm.

13. Composition according to claim 1 wherein the metal oxides are titanium, cerium, zirconium, zinc or iron oxides, or mixtures thereof.

14. Composition according to claim 1 wherein the metal oxide is titanium dioxide.

15. Composition according to claim 1 wherein the metal oxide nanopigments are coated pigments which have undergone one or more chemical, electronic, mechanochemical or mechanical surface treatments with amino acids, beeswax, fatty acids, fatty alcohols, anionic surfactants, lecithins, sodium, potassium, zinc, iron or aluminium salts of fatty acids, sodium hexametaphosphate, metal alkoxides, polyethylenes, silicones, proteins, alkanolamines, silicon oxides or metal oxides.

16. Composition according to claim 15, wherein the coated metal oxide nanopigment titanium dioxide pigments coated with silica, with silica and alumina, with silica and iron oxide, with alumina, with alumina and aluminium stearate, with alumina and aluminium laurate, with iron oxide and iron stearate, with zinc oxide and zinc stearate, with triethanolamine, with stearic acid, with sodium hexametaphosphate, with octyltrimethylsilane, with polydimethylsiloxane, with polymethylhydrogenosiloxane, with alumina and silicone, with silica and alumina and silicone, or with silica and alumina and aluminium stearate and silicone.

17. Composition according to claim 1 wherein metal oxide nanopigment is present in concentrations ranging from 0.1 to 20% by weight, relative to the total weight of the composition.

18. Composition according to claim 1 wherein the composition has a pH ranging from 3.5 to 11.

19. Composition according to claim 1 wherein the composition is in the form of an emulsion, a lotion, a gel, a vesicle dispersion, a paste or a powder or is packaged as an aerosol and is in the form of a mousse or a spray.

20. Composition according to claim 19, wherein the composition is in the form of an emulsion.

21. Composition according to claim 1 wherein the cosmetically acceptable medium consists of water or of water and at least one organic solvent selected from the group consisting of hydrophilic, lipophilic and amphiphilic organic solvents, and mixtures thereof.

22. Composition according to claim 1, further comprising at least one fatty substance, gelling and/or thickening agent, anionic polymer other than the acrylic terpolymer defined in claim 1, surfactant, moisturizer, emollient, sunscreen, metal oxide pigment, hydrophilic or lipophilic active agent, anti-free-radical agent, sequestering agent, antioxidant, preserving agent, acidifying or basifying agent, fragrance, filler, dyestuff, silicone or reducing agent.

23. Cosmetic, non-therapeutic treatment process for protecting keratinous material comprising applying an effective amount of a composition as defined in claim 1 to the keratinous material.

24. Composition according to claim 1, wherein the acrylic terpolymer comprises about 25 to 55% by weight of the carboxylic acid containing α,β-monoethylenic unsaturation, about 30 to 65% by weight of the non-surfactant monomer containing monoethylenic unsaturation and about 10 to 50% by weight of the nonionic urethane monomer.

25. Composition according to claim 9, wherein $R^1$ is a linear $C_{20}$–$C_{24}$ alkyl radical of plant origin.

26. Composition according to claim 25, wherein the alkyl radical of plant origin is the docosyl radical.

27. Composition according to claim 10, wherein the concentration of acrylic terpolymer is from 0.1 to 5% by weight.

28. Composition according to claim 17, wherein the concentration of metal oxide nanopigment is from 0.5 to 10% by weight.

29. Composition according to claim 18, wherein the pH range is from 5.5 to 8.5.

30. Composition according to claim 20, wherein the emulsion is a cream-gel.

31. Process according to claim 23, wherein the keratinous material is skin, hair, eyelashes, eyebrows or mucous membranes.

* * * * *